United States Patent [19]
Chang et al.

[11] Patent Number: 6,038,019
[45] Date of Patent: Mar. 14, 2000

[54] METHOD FOR MONITORING DEFECTS OF SEMICONDUCTOR DEVICE

[75] Inventors: Hwan-suk Chang; Hong-bae Moon, both of Kyungki-do, Rep. of Korea

[73] Assignee: Samsung Electronics Co., Ltd., Suwon, Rep. of Korea

[21] Appl. No.: 09/084,229

[22] Filed: May 26, 1998

[30] Foreign Application Priority Data

Sep. 24, 1997 [KR] Rep. of Korea ........................ 97-48557

[51] Int. Cl.[7] .................................................. G01B 11/00
[52] U.S. Cl. ...................................... 356/237.3; 356/243.6
[58] Field of Search ........................... 356/237.2, 237.3, 356/243.4, 243.6

[56] References Cited

U.S. PATENT DOCUMENTS

| | | |
|---|---|---|
| 4,377,340 | 3/1983 | Green et al. . |
| 4,641,963 | 2/1987 | Levine . |
| 4,831,274 | 5/1989 | Kohno et al. . |
| 4,871,257 | 10/1989 | Suzuki et al. . |
| 4,898,471 | 2/1990 | Stonestrom et al. . |
| 5,798,193 | 8/1998 | Pierrat et al. ............................... 430/5 |

*Primary Examiner*—Richard A. Rosenberger
*Attorney, Agent, or Firm*—Jones Volentine, L.L.P.

[57] ABSTRACT

A method for precisely monitoring defects on a semiconductor device includes inserting, into a predetermined region of a photomask used for manufacturing a semiconductor device on a semiconductor wafer, a reference defect pattern with a predetermined distribution of defects with varying sizes. Then the method involves forming reference defects on the semiconductor wafer using the photomask having the reference defect pattern. Next, control settings of a defect detection device are selected such that an output distribution of defects most closely matches the predetermined distribution of defects. Finally, defects in an integrated circuit chip region of the semiconductor wafer are monitored with the defect detection device, using the control settings selected during the selecting step.

6 Claims, 2 Drawing Sheets

METHOD FOR MONITORING DEFECTS OF SEMICONDUCTOR DEVICE

BACKGROUND OF THE INVENTION

1. Field of the Invention

The present invention relates to a method for precisely detecting defects such as particles or defective patterns formed on a semiconductor device.

2. Description of the Related Art

In general, as semiconductor devices become more highly integrated, reducing defects such as particles or defective patterns becomes as important as the fabrication processes in order to maximize yield. Therefore, it is important to provide optimal conditions during each unit process to produce fewer defects, and also to exactly monitor any defects formed on the semiconductor wafer during each unit process. Accordingly, various detection devices are used for monitoring defects generated before, during or after each unit process.

In general, the detection devices shine a light on the semiconductor device and measure the intensity of returned light (i.e., scattered or reflected light) to detect defects. After a unit process, defects are monitored on either a test wafer or a production wafer by varying the drive conditions, i.e., the control settings, of a defect detection device as appropriate for that particular unit process (process type or formed film type). The control settings must be varied to optimize the ability of the device to detect defects, because both the character of light returned from correct structures and also the character of light returned from defects vary after different process steps. The control settings of the detection devices must be selected to detect as many actual defects as possible and avoid false detections in which correct structures are classified as defects.

However, it is difficult to select the optimal values for control settings to detect defects of a given type and size; it is also difficult to determine what percentage of defects are being detected, i.e., the detection sensitivity, for a single device; and, more particularly, it is difficult to select the control settings of several devices to obtain comparable detection sensitivities among all the devices.

Although the detection devices are equipped with various functions such as self calibration for the purpose of increasing the expected reliability of detection, experience shows that the actual reliability of detection can deteriorate greatly in spite of such functions.

SUMMARY OF THE INVENTION

To solve the above problems and other disadvantages from the conventional use of defect detection devices, it is an object of the present invention to provide a method for more precisely detecting defects on a semiconductor device.

In accordance with the present invention, a method for monitoring defects on the semiconductor device includes inserting, in a predetermined region of a photomask used for manufacturing a semiconductor device on a semiconductor wafer, a reference defect pattern with a predetermined distribution of defects with varying sizes. Then reference defects are formed on the semiconductor wafer using the photomask having the reference defect pattern. The control settings of a defect detection device are selected so that an output distribution of defects most closely matches the predetermined distribution of defects. Finally, defects in an integrated circuit chip region of the semiconductor wafer are monitored with the defect detection device, using the control settings selected during the selecting step.

According to the present invention, defects formed on the integrated circuit chip region can be detected more precisely during the fabrication of semiconductor devices.

BRIEF DESCRIPTION OF THE DRAWINGS

The present invention is described with reference to the attached drawings in which.

DESCRIPTION OF THE PREFERRED EMBODIMENTS

Figure 1:
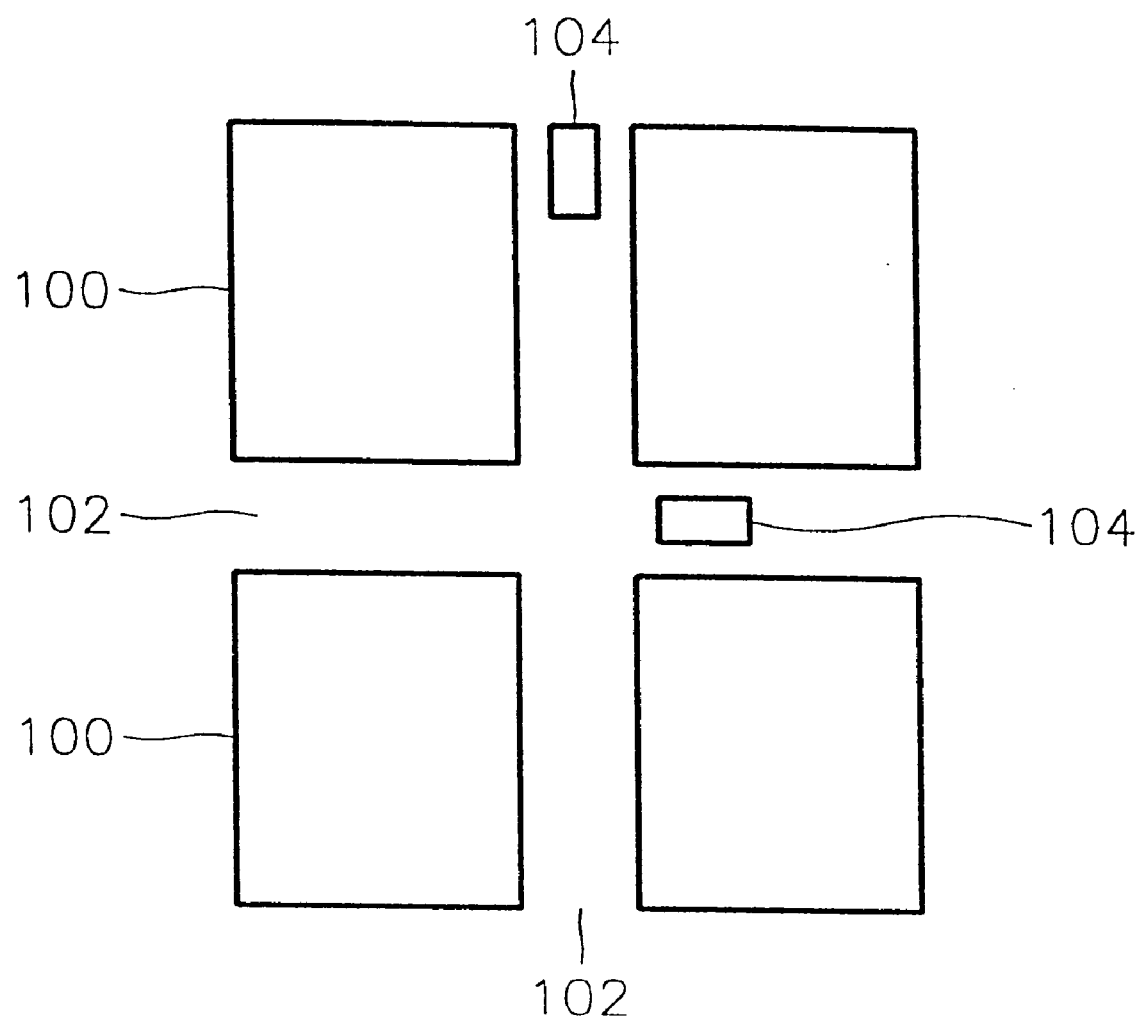
FIG. 1 is a schematic plan view of a photomask having a reference defect pattern for forming a predetermined distribution of defects on a semiconductor wafer, according to the present invention.

FIG. 1 is a schematic diagram of a photomask for the present invention. Like a conventional photomask, the photomask of the present invention has chip regions 100 in which patterns for an integrated circuit chip are recorded, and scribe lanes 102 which separate the integrated circuit chip regions. Later, the photomask is projected onto a semiconductor wafer coated with photoresist; and, the wafer is exposed to light, developed and etched to form a physical layer of a certain material in the desired pattern on the wafer. This constitutes a unit process. Other unit processes follow until the circuit is completed by the successive layering of different materials in different patterns. The scribe lanes 102 on the wafer become a cutting area for separating integrated circuit chip areas 100 during die sawing for chip packaging.

Unlike a conventional photomask, the photomask of the present invention also has a reference defect region 104. In the preferred embodiment, the reference defect pattern 104 is formed in the scribe lane area 102. The pattern in the reference defect region 104 is formed to produce defects with a range of sizes and types. That is, the reference defect pattern produces a predetermined distribution of defects with a certain number of each defect size and defect type. In the preferred embodiment, the reference defect pattern produces structures matching the sizes and types of particles and other defective structures expected before, during, or after the unit process associated with the photomask. That is, in the preferred embodiment, the predetermined distribution of defects is chosen to mimic the distribution of expected defects.

Figure 2:
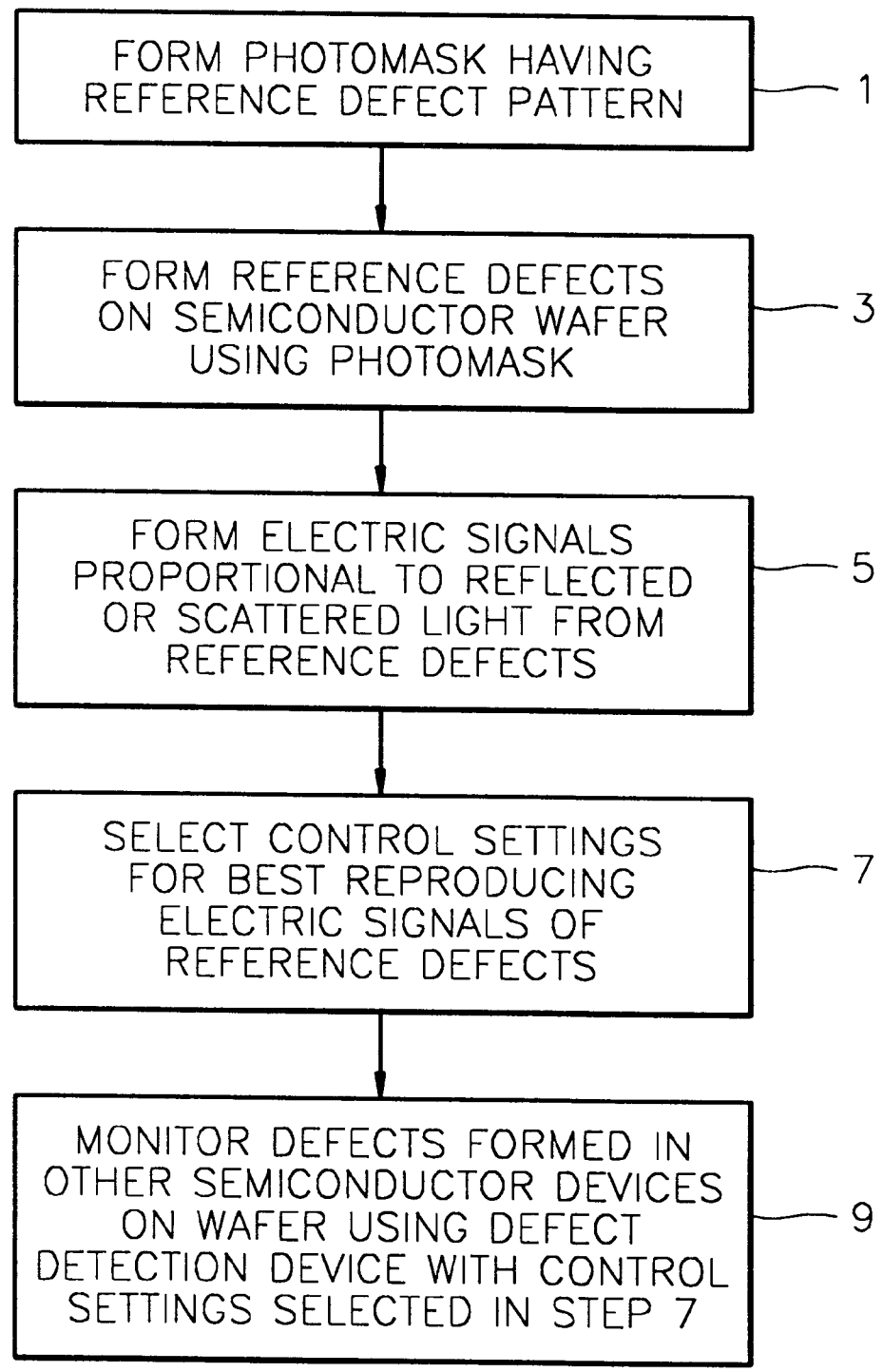
FIG. 2 is a flowchart illustrating a defect monitoring method for a semiconductor device according to the present invention.

Referring to FIG. 2, the present invention begins with forming a photomask having a reference defect pattern (step 1). Later, the photomask of the present invention is projected onto a semiconductor wafer coated with photoresist; and, the wafer is exposed to light, developed and etched, to form a reference defect pattern on the semiconductor wafer (step 3) along with the integrated circuit pattern. In the preferred embodiment, the defect pattern is formed in the scribe lane 102 (FIG. 1) of the semiconductor wafer.

Subsequently, the light of the defect detection device is radiated onto the semiconductor wafer. The device is focused on the reference defect region of the wafer to collect the returned light, i.e., the light that has been reflected or scattered by the reference defect region of the wafer. In the preferred embodiment, the light is a collimated beam and the reference defect region is in the scribe lane of the semiconductor wafer.

Then, in the method of the present invention, an electric signal proportional to the intensity of the returned light is generated as the reference defect region is sampled (step 5). The control settings of the defect detection device are varied until the electric signal produced for the reference defect region indicates as close as is possible to the correct number or location or types of defects (step 7). That is, the control settings are varied until the defect detection device gives a output distribution of defects that matches as closely as possible the predetermined distribution of defects. The control settings that best reproduce the desired defect distribution in the reference defect region are then selected as the control settings for detecting defects in the integrated circuit chips on the same wafer. Additionally, these optimal selections for the control settings can be used for the detection of defects in the integrated circuit cell patterns of other wafers going through the same unit process, even though those wafers do not have reference defect regions (step 9).

A semiconductor device is manufactured by stacking various layers on one semiconductor wafer through a sequence of many photolithographic unit processes. Accordingly, the defect detection method according to the present invention can be employed either for all patterns of each layer or only for patterns of important layers. In either case, excessively defective wafers can be intercepted between unit processes and removed from the production line before wasting further production resources. This method thereby reduces the cost of fabricating semiconductor chips.

As described above, control settings of a defect detection device are selected according to the electric signal obtained from the reference defect region formed intentionally on a semiconductor wafer, so that defects generated in the integrated circuit chip area of the semiconductor wafer can be detected more precisely. In the preferred embodiment, the reference defect region is located in the scribe lane of the wafer and the defect detection device uses a collimated beam of light.

It should be understood that the invention is not limited to the illustrated embodiments and that many changes and modifications can be made by a person skilled in the art without exceeding the scope or spirit of the present invention as defined by the appended claims and their equivalents.

What is claimed is:

1. A method for monitoring defects on a semiconductor device, comprising:

inserting, into a predetermined region of a photomask used for manufacturing a semiconductor device on a semiconductor wafer, a reference defect pattern with a predetermined distribution of defects with varying sizes;

forming reference defects on the semiconductor wafer using the photomask having the reference defect pattern;

selecting control settings of a defect detection device such that an output distribution of defects most closely matches the predetermined distribution of defects; and monitoring defects in an integrated circuit chip region of the semiconductor wafer, with the defect detection device, using the control settings selected during the selecting step, wherein during the inserting, the predetermined region is within a scribe lane, and the reference defect pattern is indicative of an expected distribution of defects found in semiconductor devices.

2. The method of claim 1, said selecting further comprising:

radiating light from a light source of the defect detection device onto the semiconductor wafer;

collecting returned light from the reference defects;

measuring an intensity of the returned light; and generating an electric signal proportional to the intensity of the returned light.

3. The method of claim 2, wherein during said radiating, the light source is a collimated beam light source.

4. The method of claim 2, wherein during said collecting, the defect detection device is focused on the reference defects.

5. The method of claim 2, said selecting further comprising computing the output distribution of defects from the electric signal proportional to the intensity of the returned light.

6. The method of claim 5, wherein during said computing, an output electrical signal from the defect detection device is approximately equal to the electrical signal proportional to the intensity, and is indicative of the output distribution of defects.

* * * * *